(12) United States Patent
Bloms-Funke et al.

(10) Patent No.: US 7,342,133 B2
(45) Date of Patent: Mar. 11, 2008

(54) SUBSTITUTED AMINO COMPOUNDS AS 5-HT/NA UPTAKE INHIBITORS

(75) Inventors: Petra Bloms-Funke, Wuerselen (DE); Elmar Friderichs, Stolberg (DE); Ivars Graudums, Stolberg (DE); Hagen-Heinrich Hennies, Simmerath (DE); Achim Kless, Aachen (DE); Klaus Schiene, Duesseldorf (DE); Oswald Zimmer, Wuerselen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 11/653,222

(22) Filed: Jan. 16, 2007

(65) Prior Publication Data

US 2007/0185212 A1 Aug. 9, 2007

Related U.S. Application Data

(63) Continuation of application No. PCT/EP2005/007537, filed on Jul. 12, 2005.

(30) Foreign Application Priority Data

Jul. 16, 2004 (DE) ............. 10 2004 034 619

(51) Int. Cl.
*C07C 211/25* (2006.01)
*A61K 31/135* (2006.01)

(52) U.S. Cl. .............. 564/336; 564/337; 564/409; 514/649; 514/650

(58) Field of Classification Search ............... None
See application file for complete search history.

(56) References Cited

U.S. PATENT DOCUMENTS

2003/0166708 A1 9/2003 Zimmer et al.

2005/0090553 A1 4/2005 Shapiro

FOREIGN PATENT DOCUMENTS

DE 100 33 459 A1 1/2002
JP 52-83818 7/1977

OTHER PUBLICATIONS

Database CAPLUS on STN, Acc. No. 1978:22336, Sawa et al., JP 52083818 (Jul. 13, 1977) (abstract).*
Database CAPLUS on STN, Acc. No. 2003:42231, Sundermann et al., WO 2003004452 (Jan. 16, 2003) (abstract).*
Sorbera et al., "Duloxetine Oxalate", Drugs Of The Future, BD. 25, Nr. 9, 2000, p. 907-916, XP002350273.
Berman et al., "Monoamine Depletion in Unmedicated Depressed Subjects", Biological Psychiatry, Bd. 51, 2002, p. 469-473, XP002350274.
International Search Report dated Nov. 24, 2005 with English translation of relevant portion (Eight (8) Pages).
German Search Report dated Dec. 9, 2005 with English translation of relevant portion (Eight (8) Pages).
Form PCT/ISA/237 dated Jan. 2004 with an English translation (Eleven (11) pages).

* cited by examiner

*Primary Examiner*—Brian Davis
(74) *Attorney, Agent, or Firm*—Crowell & Moring LLP

(57) ABSTRACT

The invention relates to substituted amino compounds, to processes for their preparation, to pharmaceutical formulations containing these compounds and to the use of these substances in the preparation of pharmaceutical formulations, especially for the treatment or inhibition of depression, anxiety, pain and urinary incontinence, and to related methods of treating or inhibiting these disorders.

14 Claims, No Drawings

SUBSTITUTED AMINO COMPOUNDS AS 5-HT/NA UPTAKE INHIBITORS

CROSS-REFERENCE TO RELATED APPLICATIONS

This application is a continuation of International patent application Ser. No. PCT/EP2005/007537 filed Jul. 12, 2005 which claims benefit to German patent application Ser. No. 10 2004 034 619.4 filed Jul. 16, 2004, the entire disclosures of which are hereby incorporated in their entirety.

FIELD OF THE INVENTION

The invention relates to substituted amino compounds, to processes for their preparation, to pharmaceutical formulations containing these compounds and to the use of these substances in the preparation of pharmaceutical formulations, especially for the treatment or alleviation of depression, anxiety, pain and urinary incontinence, and to methods of treating these disorders.

BACKGROUND OF THE INVENTION

The monoamine reuptake inhibitors from the class of the tricyclic antidepressants (TCAs) have been used successfully in the treatment of depression since the 1960s. The relevance of dysfunctions of the monoaminergic systems in psychiatric disorders is widely recognised on account of the pre-clinically and clinically proven antidepressant activities of TCAs, selective serotonin reuptake inhibitors (so-called SSRIs), selective noradrenaline reuptake inhibitors, mixed serotonin and noradrenaline reuptake inhibitors (so-called SNRIs), monoamineoxidase inhibitors and modulators of various serotonin and noradrenaline receptor subtypes (Berman et al., Biol Psychiatry, 2002 Mar 15; 51(6): 469-73). In addition, antidepressants are important adjuvants in the therapy of pain, especially in the case of chronic pain. However, monoamine reuptake inhibitors also induce an independent analgesic activity by activating the decreasing inhibition of spinal nociceptive signals. Successes in the treatment of urinary incontinence by the use of monoamine reuptake inhibitors have also been described (Sorbera et al., Drugs of the future, 2000, Vol 25, page 907-916). Monoamine reuptake inhibitors are additionally suitable for the treatment of anxiety, fibromyalgia, eating disorders, bulimia, hyperactivity (attention deficit hyperactivity disorder; ADHD), drug dependency, addiction and withdrawal, trichotillomania, skin diseases such as post-herpetic neuralgia and pruritus, memory disorders, cognitive disorders and Alzheimer's disease.

The therapeutic use of the previously-known antidepressants is limited by the undesirable side-effects that frequently occur. Particular mention may be made here of constipation, urinary retention, dryness of the mouth, accommodation disturbances, orthostatic hypotension with tachycardia, sedation, serotonin syndrome, sexual dysfunctions, dizziness, cognitive dysfunctions and QT lengthening including torsade de pointes. In the treatment of psychiatric disorders, a late onset of action, a high rate of relapse and an absence of action in 20-30% of patients are disadvantageous.

SUMMARY OF THE INVENTION

One object of the invention is to provide novel potent monoamine reuptake inhibitors having therapeutically relevant active components in depression, anxiety, pain and urinary incontinence. The activities should be based in a decisive manner on the inhibition of the reuptake of serotonin (5-HT), of noradrenaline (NA) or a combination of these mechanisms. The substances should exhibit an improved profile of action and better tolerability.

It has now been found that compounds corresponding to formula I bring about a marked inhibition of 5-HT and NA reuptake.

The present invention accordingly provides amino compounds corresponding to formula I

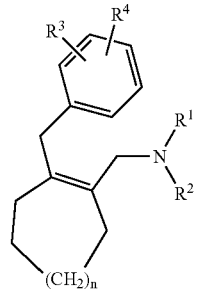

I in which
R$^1$ represents a straight-chained or branched C$_{1-4}$-alkyl group,
R$^2$ represents hydrogen or the radical R$^1$,
R$^3$ and R$^4$, independently of one another, represent the group R$^2$, Cl, F, Br, the radical OR$^2$, CF$_3$, OCF$_3$, OCH$_2$F, OCHF$_2$, or
R$^3$ and R$^4$ together represent a methylenedioxy group or a fused benzo group which is optionally substituted by the group R$^2$, Cl, F, Br, the radical OR$^2$, CF$_3$, OCF$_3$, OCH$_2$F or OCHF$_2$,
and n=0, 2 or 3.

The compounds according to the invention may be either in the form of the free bases or in the form of pharmaceutically acceptable salts.

Preference is given to compounds in which R$^1$ represents methyl, R$^2$ represents hydrogen or methyl and R$^3$ and R$^4$ represent hydrogen or Cl, and n=0, 2 or 3.

Particular preference is given to the following compounds according to the invention and their salts:
[2-(4-chlorobenzyl)-cyclohept-1-enylmethyl]-dimethylamine and the corresponding hydrochloride (1)
[2-(4-chlorobenzyl)-cyclopent-1-enylmethyl]-dimethylamine and the corresponding hydrochloride (2a)
[2-(4-chlorobenzyl)-cyclooct-1-enylmethyl]-dimethylamine and the corresponding hydrochloride (2b)
[2-(4-chlorobenzyl)-cyclohept-1-enylmethyl]-methylamine and the corresponding hydrochloride (3).

The invention also provides a process for the preparation of the substituted amino compounds of the general formula I, which process is characterised by the reaction of tertiary alcohols of the general formula II

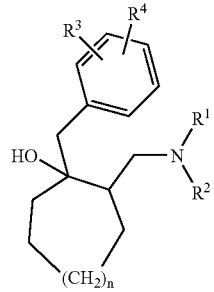

II wherein R$^1$ to R$^4$ and n have the same meaning as in formula I, with semi-concentrated or concentrated organic or inorganic acids, especially hydrobromic acid, in a temperature range of from 0° C. to 130° C., the tertiary alcohols of the general formula II being obtained by reaction of β-amino ketones of the general formula III

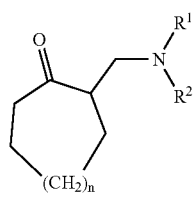

wherein $R^1$, $R^2$ and n have the same meaning as in formula I, with an organometallic compound of formula IV

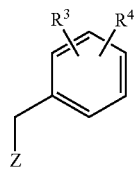

in which Z represents MgCl, MgBr, MgI or Li and $R^3$ and $R^4$ are as defined above.

The reaction of compounds III and IV is carried out in an aliphatic ether, for example diethyl ether and/or tetrahydrofuran, at temperatures of from −70° C. to +60° C. Compounds of formula IV in which Z represents a lithium atom are obtained from compounds of formula IV in which Z represents Br or I by halogen-lithium exchange by means of, for example, an n-butyllithium/n-hexane solution.

If $R^3$ and/or $R^4$ in compounds of the general formula I represent(s) a methoxy radical, it is possible to prepare compounds of formula I in which $R^3$ and/or $R^4$ represent(s) a hydroxy group by reaction with diisobutylaluminium hydride in an aromatic hydrocarbon such as toluene or xylene at a temperature of from 60° C. to 130° C.

It is also possible to obtain such compounds directly from compounds of formula II in which $R^3$ and/or $R^4$ represent(s) $OCH_3$, by heating compounds of formula II at reflux with a solution of hydrogen bromide in glacial acetic acid.

Compounds of the general formula I in which $R^2$ represents hydrogen are obtainable from corresponding compounds of formula I wherein $R^2$=methyl by heating with chloroformic acid phenyl ester followed by basic hydrolysis, for example with sodium hydroxide solution in higher boiling alcohols such as ethylene glycol.

The compounds of formula I can be converted into their salts in a manner known per se with physiologically acceptable acids such as hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid and/or aspartic acid. The salt formation is preferably carried out in a solvent such as diisopropyl ether, alkyl acetate, acetone and/or 2-butanone. For the preparation of the hydrochlorides, trimethylchlorosilane in aqueous solution is particularly suitable.

The substituted amino compounds of the general formula I according to the invention are toxicologically harmless and are therefore suitable as pharmaceutical active ingredients in pharmaceutical formulations.

The present invention therefore further provides pharmaceutical formulations comprising at least one substituted amino compound of the general formula I according to the invention and, optionally, physiologically acceptable auxiliary substances. The pharmaceutical formulations according to the invention are preferably suitable for the control of pain (in particular chronic pain, neuropathic pain, inflammatory pain), migraine, fibromyalgia and for the treatment, inhibition or prophylaxis of depression (unipolar, severe depression with and without mania, moderate depression, slight depression, melancholia, bipolar depression; bipolar disorders I (mania and severe depression), bipolar disorders II (hypomania and severe depression), cyclothymic personality disorders (hypomania and mild depression), anxiety (subtypes generalised anxiety, panic attacks, obsessive compulsive disorders, social anxiety disorder, phobias, PSTD), sleep disorders, urinary incontinence (stress and urge), eating disorders, bulimia, hyperactivity (attention deficit hyperactivity disorder; ADHD), drug dependency, addiction and withdrawal, trichotillomania, skin diseases such as postherpetic neuralgia and pruritus, memory disorders, cognitive disorders, psychoses and/or Alzheimer's disease.

The present invention relates also to the use of at least one substituted amino compound of the general formula I in the preparation of a medicament for the control of pain (in particular chronic pain, neuropathic pain, inflammatory pain), migraine, fibromyalgia and for the treatment, inhibition or prophylaxis of depression (unipolar, severe depression with and without mania, moderate depression, slight depression, melancholia, bipolar depression; bipolar disorders I (mania and severe depression), bipolar disorders II (hypomania and severe depression), cyclothymic personality disorders (hypomania and mild depression), anxiety (subtypes generalised anxiety, panic attacks, obsessive compulsive disorders, social anxiety disorder, phobias, PSTD), sleep disorders, urinary incontinence (stress and urge), eating disorders, bulimia, hyperactivity (attention deficit hyperactivity disorder; ADHD), drug dependency, addiction and withdrawal, trichotillomania, skin diseases such as postherpetic neuralgia and pruritus, memory disorders, cognitive disorders, psychoses and/or Alzheimer's disease.

The pharmaceutical formulations according to the invention may be present in the form of liquid, semi-solid or solid medicament forms, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, and may also be administered as such.

In addition to at least one substituted amino compound of the general formula I according to the invention, the pharmaceutical formulations according to the invention usually comprise further physiologically acceptable pharmaceutical auxiliary substances, which are preferably selected from the group consisting of carriers, fillers, solvents, diluents, surface-active substances, colorings, preservatives, disintegrators, glidants, lubricants, flavourings and binders.

The choice of physiologically acceptable auxiliary substances and the amounts thereof to be used are dependent on whether the medicament is to be administered orally, subcutaneously, parenterally, intravenously, intraperitoneally, intradermally, intramuscularly, intranasally, buccally, rectally or locally, for example to infections of the skin, the mucous membranes and to the eyes. Formulations in the form of tablets, dragees, capsules, granules, pellets, drops, juices and syrups are suitable for oral administration; solutions, suspensions, readily reconstitutable dry formulations and sprays are suitable for parenteral and topical administration and for administration by inhalation. Compounds of the general formula I according to the invention in a depot, in dissolved form or in a plaster, optionally with the addition of agents which promote penetration through the skin, are suitable formulations for percutaneous administration. Preparation forms which can be used orally or percutaneously can also release the compounds of the general formula I according to the invention in a delayed manner.

The preparation of the pharmaceutical formulations according to the invention can be carried out with the aid of conventional agents, devices, methods and processes known to the person skilled in the art, as are described, for example, in A. R. Gennaro (ed.), Remington's Pharmaceutical Sciences, 17th Edition, Mack Publishing Company, Easton, Pa. (1985), especially in Part 8, Chapters 76 to 93. The corresponding literature description is incorporated herein by reference and is to be regarded as part of the disclosure.

The amount of the particular compound of the general formula I according to the invention to be administered to the patients can vary and is dependent, for example, on the weight or age of the patient and on the mode of administration, the indication and the severity of the disorder. From 0.005 to 500 mg/kg, preferably from 0.05 to 5 mg/kg body weight of the patient of at least one substituted amino compound of the general formula I according to the invention are usually administered.

The invention also relates further to methods of treating depression, pain and urinary incontinence, in which methods the compounds according to the invention are employed.

EXAMPLES

The following examples are provided to illustrate the process according to the invention in greater detail and do not and should not be understood to limit the claims appended hereto. The invention is not limited in its application to the details of any particular formulation shown, since the invention is capable of other embodiments.

Silica gel 60 (0.040-0.063 mm) from E. Merck, Darmstadt, was Employed as the Stationary Phase for the Column Chromatography.

Example 1

[2-(4-Chlorobenzyl)-cyclohept-1-enylmethyl]-dimethylamine; hydrochloride

Step 1:

1-(4-Chlorobenzyl)-2-dimethylaminomethyl-cycloheptanol

A solution of 32.00 g of 2-dimethylaminomethylcycloheptanone in 190 ml of absolute diethyl ether was added dropwise at 20° C., with stirring, to a freshly prepared solution of the Grignard reagent comprising 6.17 g of magnesium turnings and 40.50 g of 4-chlorobenzyl chloride in 500 ml of absolute diethyl ether. When the addition was complete, stirring was continued for a further 2 hours at 20° C. Decomposition was then effected, while cooling with ice, by the dropwise addition of 100 ml of a saturated ammonium chloride solution followed by 200 ml of distilled water. The organic phase was separated off, and the aqueous phase was extracted twice using 200 ml of ethyl acetate each time. The combined organic extracts were washed with saturated sodium chloride solution, dried over sodium sulfate and concentrated by evaporation in vacuo. The oily residue was purified by column chromatography with ethyl acetate as eluant, 39.69 g of the title compound being obtained in the form of the free base. This was dissolved in 270 ml of 2-butanone and converted into the hydrochloride by addition of 2.8 ml of water and 17.4 ml of trimethylchlorosilane. 37.30 g (59.4% of theory) of the title compound as a diastereoisomeric mixture were obtained in the form of colorless crystals.

Melting Point: 235-237° C.

Step 2:

[2-(4-Chlorobenzyl)-cyclohept-1enylmethyl]-dimethylamine; hydrochloride 33.23 g of the product from Step 1 were heated at reflux for 1 hour in 140 ml of hydrobromic acid (47% HBr). The mixture was then concentrated by evaporation in vacuo and the residue was recrystallised from ethanol. After converting the product into the free base with aqueous sodium carbonate solution, 9.35 g (29.8% of theory) of the title compound were obtained therefrom in the form of colorless crystals by hydrochloride precipitation with trimethylchlorosilane/water in 2-butanone as described in Step 1.

Melting Point: 220-222° C.

Example 2

Following the procedure described in Example 1 and using 2-dimethylaminomethyl-cyclopentanone or 2-dimethylaminomethyl-cyclooctanone instead of the corresponding cycloheptanone derivative in Step 1, the following were obtained in an analogous manner:

a) [2-(4-chlorobenzyl)-cyclopent-1-enylmethyl]-dimethylamine; hydrochloride melting point: 191° C.

b) [2-(4-chlorobenzyl)-cyclooct-1enylmethyl]-dimethylamine; hydrochloride melting point: 234-237° C.

Example 3

[2-(4-Chlorobenzyl)-cyclohept-1enylmethyl]-methylamine; hydrochloride 0.19 g of the product from Example 1 in the form of the free base was heated at reflux for 2 hours with 0.1 ml of chloroformic acid phenyl ester in 12 ml of anhydrous toluene. After cooling, washing was carried out with, in succession, 2.5 N sodium hydroxide solution, water, 1N hydrochloric acid or a saturated sodium chloride solution, followed by drying over sodium sulfate. Concentration by evaporation was carried out in vacuo, and the resulting residue was taken up in 6 ml of ethylene glycol and heated for 4.5 hours at 110° C. with 1.4 ml of 5N sodium hydroxide solution. After cooling, the mixture was diluted with 20 ml of water and extracted three times using 10 ml of dichloromethane each time. The extracts were washed with saturated sodium chloride solution and dried over sodium sulfate. Concentration by evaporation was carried out in vacuo, and the resulting oily residue was converted into the hydrochloride in the manner described in Example 1, Step 1, using trimethylchlorosilane/water in 2-butanone. 0.08 g (39% of theory) of the title compound was obtained in the form of virtually colorless crystals.

$^1$H-NMR (DMSO-d$_6$): 1.12-1.70 (m, 6H), 2.04-2.13 (m, 2H); 2.30-2.38 (m, 2H); 2.71 (s, 3H); 3.53 (s, 2H); 3.82-3.90 (m, 2H); 7.13-7.40 (m, 4H).

Pharmacological Studies a) Studies of the inhibition of 5-HT and NA reuptake

In order to be able to carry out these in vitro studies, synaptosomes are freshly isolated from areas of rat brain. A so-called "P$_2$" fraction is used in each case, which is prepared exactly according to the procedure of Gray, E. G. and Whittaker, V. P. (J. Anat. 76, 79-88, 1962). For NA reuptake, these vesicular particles are isolated from the hypothalamus of male rat brains, and for 5-HT reuptake, they are isolated from the medulla +pons region.

The following characteristic data were determined for the NA and 5-HT reuptake:

NA uptake: Km=0.32±0.11 µM

5-HT uptake: Km=0.084±0.011 µM (in each case N=4, i.e. mean values ± SEM from 4 independent test series which were carried out in triplicate parallel tests).

A detailed description of the method can be found in the publication of Frink, M., Hennies, H. H., Englberger, W. et al. (Arzneim.-Forsch./Drug Res. 46 (III), 11, 1029-1036, 1996) (the batch can also be carried out on microtitre plates (250 µl/well) at room temperature).

Evaluations:

In addition to % inhibitions at fixed concentrations of test substance (e.g. 1×10$^{-6}$ M or 1×10$^{-5}$ M in the batch), dose dependencies were also checked. IC$_{50}$ values were obtained thereby which can be converted into inhibitor constants (K$_i$) according to the "Cheng-Prusoff equation" (Cheng, Y. C. and Prusoff, W. H., Biochem. Pharmacol. 22, 3099-3108, 1973). The IC$_{50}$ values were obtained with the aid of the "Figure P" computer program (Version 6.0, Biosoft, Cambridge, England). Km values were calculated according to Lineweaver, H. and Burk, D. (J. Am. Chem. Soc. 56, 658-666, 1934). The "Ligand" computer program (Version 4, Biosoft, England) was used to show K$_D$ values.

A dose-dependent inhibition of 5-HT and NA reuptake was determined for the compounds of Examples 1 and 2b. The corresponding results are summarised in the table below.

TABLE 1

| Compound according to Example No. | Inhibition of 5-HT reuptake; Ki (µmol./l) | Inhibition of NA reuptake; Ki (µmol./l) |
|---|---|---|
| Example 1 | 0.003 | 0.03 |
| Example 2b | 0.03 | 0.34 | b) Studies of Analgesic Activity in the Formalin Test in the Mouse

The formalin test (Dubuisson, D. and Dennis, S. G., 1977, Pain, 4, 161-174) represents a model for acute and chronic pain. In the studies presented here, the chronic pain component was evaluated.

By means of a single formalin injection into the dorsal side of a rear paw, a biphase nociceptive reaction is induced in freely mobile test animals; the reaction is assessed by observing three markedly different behaviour patterns.

Formalin is injected subcutaneously in a volume of 20 µl and a concentration of 1% into the dorsal side of the right rear paw of each animal. The specific behavioural changes differing from normal behaviour (score 0), such as lifting (score 1) and shaking of the paw (score 2), as well as biting and licking reactions (score 3), are observed and recorded continuously at 3-minute intervals for 60 minutes after the formalin injection. The behavioural changes are weighted differently (score 0-3) and a pain rate (PR) is calculated using the following formula:

$$PR=[(T_0 \times 0)+(T_1 \times 1)+(T_2 \times 2)+(T_3 \times 3)]/180,$$

where $T_0$, $T_1$, $T_2$ and $T_3$ correspond to the time, in seconds, at which the animal exhibited behaviour 0, 1, 2 or 3. The size of the group was 10 animals (n=10). On the basis of the PR calculations, the activity of the substance was determined in percent as the change relative to a control. The ED$_{50}$ was determined by means of regression analysis.

A dose-dependent inhibition of the nociceptive behaviour was observed for the compound according to Example 1. The result is shown in the following table.

TABLE 2

| Compound according to Example No. | Mode of administration | ED$_{50}$ value, mg/kg |
|---|---|---|
| Example 1 | i.v. | 4.71 | c) Studies of Analgesic Activity in the Writhing Test in the Mouse

The writhing test in the mouse is a modification of the method according to Hendershot L C, Forsaith, J, J Pharmacol Exp Ther 125: 237-240 (1959).

0.3 ml/animal of a 0.02% aqueous phenylquinone solution, with the addition of 5% ethanol, is administered intraperitoneally to the animals as pain stimulus. This solution is administered 30 minutes (test substance p.o.) or 10 minutes (test substance i.v.) after administration of the test substance. The pain-induced stretching movements (so-called writhing reactions=straightening of the body with extension of the rear extremities) are recorded 5 to 20 minutes after the administration of phenylquinone. The animals treated with the test substance are compared with a control group that received physiological saline. Size of the group n=10.

A dose-dependent inhibition of the nociceptive behaviour was observed for the compound according to Example 1. The result is shown in the following table.

TABLE 3

| Compound according to Example No. | Mode of administration | ED$_{50}$ value, mg/kg |
|---|---|---|
| Example 1 | i.v. | 3.04 | d) Study of Antidepressant Activity in the Forced Swimming Test (Porsolt Test) in the Mouse The studies to determine the antidepressant activity of the compounds of formula I according to the invention were carried out in the forced swimming test (Porsolt test) in the mouse (Porsolt, R. et al., Arch. Int. Pharmacodyn. Vol. 229, p. 327-336 (1977)). Male mice (20-25 g body weight) were placed individually for a period of 6 minutes into a flat water tank from which they were unable to escape and accordingly were forced to swim. After some time, the animals gave up their attempts to swim and entered a phase of immobility. In the interval of from 2 to 6 minutes after introduction of the animal, the duration of the phase of immobility was determined. Test substance and vehicle groups each comprise 10 animals. Changes in the duration of the phase of immobility are stated relative to the vehicle control.

Antidepressants induce a shortening of the phase of immobility.

A significant shortening of the phase of immobility, and accordingly an antidepressant activity, was determined in the forced swimming test for the compound according to Example No. 1. The results are shown in the following table.

TABLE 4

| Compound according to Example No. | Mode of administration | Dose mg/kg | Relative duration of the phase of immobility versus control |
|---|---|---|---|
| Example 1 | i.p. | 10 | +9% |
| Example 1 | i.p. | 21.5 | −34% |
| Example 1 | i.p. | 31.6 | −67%*** |
| Example 1 | i.p. | 46.4 | −76%*** |

Student's T test;
***p < 0.001

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A substituted amino compound corresponding formula I:

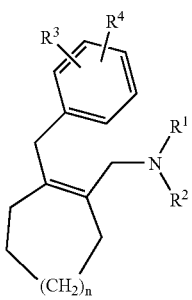

wherein
R$^1$ represents a straight-chained or branched C$_{1-4}$-alkyl group,
R$^2$ represents hydrogen or is the same as R$^1$,
R$^3$ and R$^4$, independently of one another, are the same as R$^2$, Cl, F, Br, OR$^2$, CF$_3$, OCF$_3$, OCH$_2$F, OCHF$_2$, or
R$^3$ and R$^4$ together represent a methylenedioxy group or a fused benzo group which may be substituted by R$^2$, Cl, F, Br, OR$^2$, CF$_3$, OCF$_3$, OCH$_2$F or OCHF$_2$, and
n=0, 2or 3,
or a pharmaceutically acceptable salt thereof.

2. The compound according to claim 1, wherein R$^3$ and R$^4$ together represent a methylenedioxy group or a fused benzo group which is substituted by R$^2$, Cl, F, Br, OR$^2$, CF$_3$, OCF$_3$, OCH$_2$F or OCHF$_2$.

3. The compound according to claim 1, wherein said compound is in the form of a free base.

4. The compound of claim 1, wherein R$^1$ represents methyl, R$^2$ represents hydrogen or methyl, R$^3$ and R$^4$ represent hydrogen or Cl, and n=0, 2 or 3.

5. The compound of claim 1, wherein said compound is selected from the group consisting of:
[2-(4-chlorobenzyl)-cyclohept-1-enylmethyl]-dimethylamine and the corresponding hydrochloride (1)
[2-(4-chlorobenzyl)-cyclopent-1-enylmethyl]-dimethylamine and the corresponding hydrochloride (2a)
[2-(4-chlorobenzyl)-cyclooct-1-enylmethyl]-dimethylamine and the corresponding hydrochloride (2b) and
[2-(4-chlorobenzyl)-cyclohept-1-enylmethyl]-methylamine and the corresponding hydrochloride (3).

6. A process for preparing a substituted amino compound corresponding to formula I

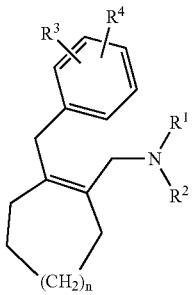

wherein
R$^1$ represents a straight-chained or branched C$_{1-4}$-alkyl group,
R$^2$ represents hydrogen or is the same as R$^1$,
R$^3$ and R$^4$, independently of one another, are the same as R$^2$, Cl, F, Br, OR$^2$, CF$_3$, OCF$_3$, OCH$_2$F, OCHF$_2$, or
R$^3$ and R$^4$ together represent a methylenedioxy group or a fused benzo group which may be substituted by R$^2$, Cl, F, Br, OR$^2$, CF$_3$, OCF$_3$, OCH$_2$F or OCHF$_2$, and
n=0, 2or 3,
or a pharmaceutically acceptable salt thereof, comprising the steps of:
reacting a tertiary alcohol corresponding to formula II

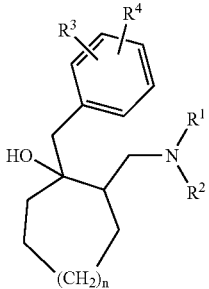

with an organic or inorganic acid at a temperature range of from 0° C. to 130° C., or
heating a tertiary alcohol of formula II in which R$^3$ and/or R$^4$ represent a methoxy group at reflux with a solution of hydrogen bromide in glacial acetic acid, and
wherein the tertiary alcohol of formula II is prepared by reacting β-amino ketones of formula III

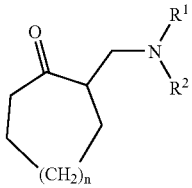

with an organometallic compound of formula IV

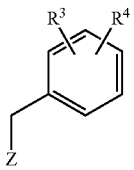

in which Z represents MgCl, MgBr, MgI or Li.

7. The process of claim 6, wherein a compound of formula I in which $R^3$ and/or $R^4$ represent a hydroxy group is prepared by reacting a compound of formula I in which $R^3$ and/or $R^4$ represent a methoxy group with diisobutyl-aluminium hydride in an aromatic hydrocarbon at from 60° C. to 130° C.

8. The process of claim 6, wherein a compound of formula I in which $R^2$ represents hydrogen is prepared from a corresponding compound of formula I wherein $R^2$ is methyl by heating with chloroformic acid phenyl ester followed by basic hydrolysis.

9. The process of claim 6, wherein the acid is hydrobromic acid.

10. The process of claim 6, wherein the reaction of compounds of formulas III and IV is carried out in an aliphatic ether at temperatures of from −70° C. to +60° C.

11. The process of claim 6, where in the compound of formula IV, Z represents a lithium atom and said compound of formula IV is obtained through a halogen-lithium exchange reaction starting with compounds of formula IV in which Z represents Br or I.

12. A pharmaceutical formulation comprising at least one compound corresponding to formula I

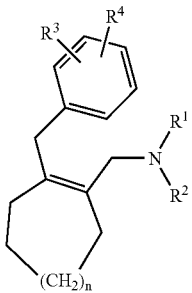

wherein $R^1$ represents a straight-chained or branched $C_{1-4}$-alkyl group, $R^2$ represents hydrogen or is the same as $R^1$, $R^3$ and $R^4$, independently of one another, are the same as $R^2$, Cl, F, Br, $OR^2$, $CF_3$, $OCF_3$, $OCH_2F$, $OCHF_2$, or $R^3$ and $R^4$ together represent a methylenedioxy group or a fused benzo group which may be substituted by $R^2$, Cl, F, Br, $OR^2$, $CF_3$, $OCF_3$, $OCH_2F$ or $OCHF_2$, and n=0, 2 or 3, or a pharmaceutically acceptable salt thereof, as an active ingredient and a physiologically acceptable auxiliary substance.

13. A method of alleviating pain, said method comprising the step of administering, to a subject in need thereof, a pharmaceutically effective amount of a compound of formula I

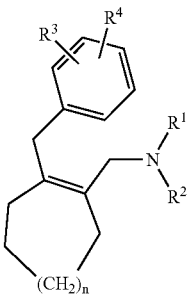

wherein $R^1$ represents a straight-chained or branched $C_{1-4}$-alkyl group, $R^2$ represents hydrogen or is the same as $R^1$, $R^3$ and $R^4$, independently of one another, are the same as $R^2$, Cl, F, Br, $OR^2$, $CF_3$, $OCF_3$, $OCH_2F$, $OCHF_2$, or $R^3$ and $R^4$ together represent a methylenedioxy group or a fused benzo group which may be substituted by $R^2$, Cl, F, Br, $OR^2$, $CF_3$, $OCF_3$, $OCH_2F$ or $OCHF_2$, and n=0, 2 or 3, or a pharmaceutically acceptable salt thereof.

14. A method of treating or inhibiting a condition or disease selected from the group consisting of depression, anxiety, urinary incontinence, fibromyalgia, eating disorders, bulimia, hyperactivity, drug dependency, addiction and withdrawal, trichotillomania, post-herpetic neuralgia, pruritus, memory disorders, cognitive disorders and/or Alzheimer's disease, said method comprising the step of administering, to a subject in need thereof, a pharmaceutically effective amount of a compound corresponding to formula I

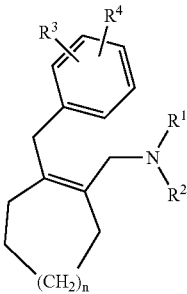

wherein $R^1$ represents a straight-chained or branched $C_{1-4}$-alkyl group, $R^2$ represents hydrogen or is the same as $R^1$, $R^3$ and $R^4$, independently of one another, are the same as $R^2$, Cl, F, Br, $OR^2$, $CF_3$, $OCF_3$, $OCH_2F$, $OCHF_2$, or $R^3$ and $R^4$ together represent a methylenedioxy group or a fused benzo group which may be substituted by $R^2$, Cl, F, Br, $OR^2$, $CF_3$, $OCF_3$, $OCH_2F$ or $OCHF_2$, and n=0, 2 or 3, or a pharmaceutically acceptable salt thereof.

* * * * *